United States Patent [19]

Rowland et al.

[11] Patent Number: 5,379,779

[45] Date of Patent: Jan. 10, 1995

[54] ZEBRA EXCHANGE GUIDEWIRE

[75] Inventors: Christopher A. Rowland, Marlboro; Earl Bardsley, Arlington; Richard DeMello, Acton, all of Mass.

[73] Assignee: Boston Scientific Corporation, Watertown, Mass.

[21] Appl. No.: 106,829

[22] Filed: Aug. 16, 1993

[51] Int. Cl.⁶ ............................................. A61B 5/00
[52] U.S. Cl. ................................. 128/772; 604/280; 604/282
[58] Field of Search .................. 128/657, 772; 604/95, 604/164, 280, 281, 282, 283, 284, 285

[56] References Cited

U.S. PATENT DOCUMENTS

| 3,094,124 | 6/1963 | Birtwell | 604/280 |
| 3,399,668 | 9/1968 | Lundgren | 604/280 X |
| 4,257,421 | 3/1981 | Beal | 128/657 X |
| 4,456,017 | 6/1984 | Miles | 604/95 X |
| 4,563,176 | 1/1986 | Gustavsson et al. | 604/280 X |
| 4,951,686 | 8/1990 | Herlitze | 128/772 |
| 5,084,022 | 1/1992 | Claude | 604/164 |
| 5,147,315 | 9/1992 | Weber | 604/164 |

OTHER PUBLICATIONS

Lumina Hydrphilic Coated Guidewire, Publication of Surgitek Corp., 1994.
Brochure: "Geenen Endotorque TM Guidewire", Microvasive ®, Boston Scientific Corporation (?).

Primary Examiner—Sam Rimell
Attorney, Agent, or Firm—Frances P. Craig

[57] ABSTRACT

An exchange guidewire for positioning and exchanging medical catheters within a bodily passage during a medical procedure which uses an endoscope. The guidewire includes a wire of a length sufficient for exchange of the catheters through the endoscope, a radiopaque flexible coil fixed to the distal end of the wire, and a pattern of stripes endoscopically discernable along the guidewire. Optionally, a shrink-wrap, low-friction sleeve jackets the guidewire, the pattern of indicia being endoscopically discernable along the length of the jacketed guidewire. The position of the exchange guidewire indicia relative to the endoscope optical lens may be monitored by viewing the stripes endoscopically. A method of positioning and exchanging medical catheters within a bodily passage during a medical procedure which uses an endoscope is also disclosed.

18 Claims, 1 Drawing Sheet

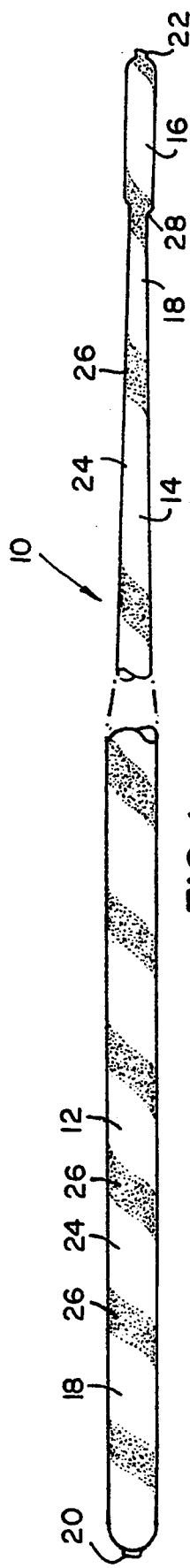
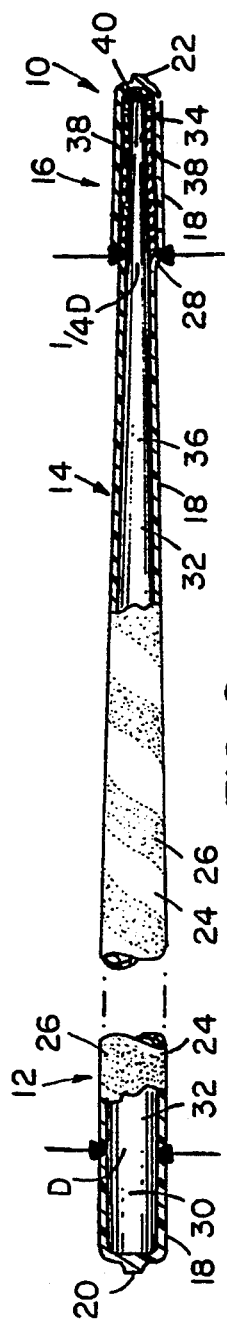
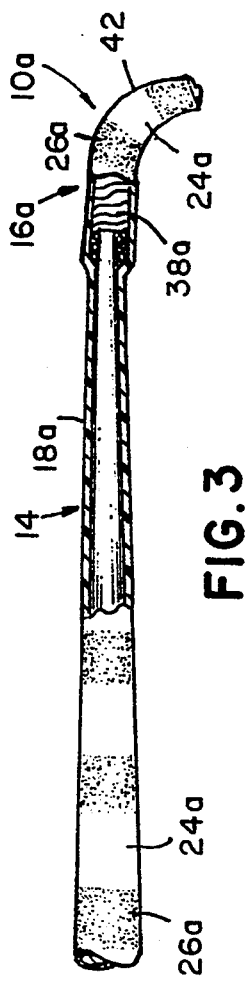
FIG. 1
FIG. 2
FIG. 3

ZEBRA EXCHANGE GUIDEWIRE

BACKGROUND OF THE INVENTION

The present invention relates to guidewires for medical devices, and particularly to exchange guidewires for endoscopic devices.

During certain endoscopic procedures an exchange guidewire is threaded through a lumen or open channel in the endoscope. The guidewire is then maneuvered into place within a bodily passage to act as a guide for positioning of medical catheter devices to perform the procedure. Exchange guidewires are known that have a flexible coil fixedly attached to one end of a core wire to aid the maneuvering of the wire into the bodily passage, and a low-friction Teflon ® sleeve covering the wire/coil combination.

Examples of an endoscopic medical procedure in which such a guidewire may be used are endoscopic surgery or other medical treatment within the common bile duct, the cystic duct, the pancreatic duct, or the left or right hepatic duct. The endoscope is introduced orally and maneuvered through the alimentary canal into the duodenum. The guidewire is threaded through the endoscope lumen and manipulated by torquing, pushing, and pulling to cannulate the papilla and to enter the common bile duct and, if necessary, any duct branching therefrom. The position of the guidewire is confirmed fluoroscopically. Typically, the flexible coil is formed from a radiopaque material to aid fluoroscopic viewing of the guidewire position. After positioning of the guidewire within the duct, a catheter bearing a medical instrument is threaded onto the exposed end of the guidewire and maneuvered through the endoscope, along the guidewire, and into position within the duct to be treated. If necessary, a sphincter tome may be threaded onto the guidewire to cut the sphincter muscle and enlarge the papilla before the guidewire enters the papilla. The guidewire, the medical instrument catheter, and the area near the papilla all are illuminated by a fiber optic light source within the endoscope and may be viewed through the endoscope using a fiber optic lens.

When a second instrument is required to perform the medical procedure, the first catheter must be withdrawn and the replacement catheter bearing the next required instrument is threaded onto the guidewire and maneuvered into position. This "exchange" process is carried out with each successive instrument needed to perform the procedure. The endoscopic system using an exchange guidewire to guide each instrument catheter into position has greatly simplified endoscopic surgery and other endoscopic procedures.

There is, however, a tendency for the guidewire to be displaced during the withdrawal of a catheter. Because such movement is not readily discerned endoscopically, the surgeon has been required to confirm the correct positioning of the guidewire tip using fluoroscopy before introducing each new instrument catheter. This can result in increased procedure time and in additional exposure of the patient and medical staff to radiation.

It would be desirable, for certain endoscopic procedures, to have a way to visually discern displacement of the guidewire during the exchange process without the use of further fluoroscopy. The exchange guidewires described herein were developed to address that need.

SUMMARY OF THE INVENTION

In one aspect, the invention is an exchange guidewire for positioning and exchanging medical catheters within a bodily passage during a medical procedure which uses an endoscope. The guidewire includes a core wire of a length sufficient for exchange of the catheters through the endoscope, a flexible coil fixed to the core wire, and a pattern of indicia endoscopically visible along at least the portion of the guidewire to be endoscopically viewed. The core wire has a proximal end about 0.01–0.05 inch in diameter and a distal end of a diameter no greater than that of the core wire proximal end. The flexible coil is about 1–10 cm long and is of a diameter between about 0.01 inch and approximately the diameter of the core wire proximal end. At least a portion of the coil and/or the core wire distal end is radiopaque. The coil is fixed to the core wire distal end to produce a wire/coil assembly.

In an alternate, narrower aspect of the invention, the flexible coil of the guidewire is radiopaque, the coil has a distal tip fixed to the core wire distal end, and a low-friction sleeve is tightly fitted around and conforms to the wire/coil assembly to cover the wire/coil assembly from the core wire proximal end to the coil distal tip to form a jacketed guidewire; and the pattern of indicia is endoscopically discernable at the surface of the jacketed guidewire along its length. The position of the indicia of either exchange guidewire relative to an optical lens of the endoscope may be monitored by viewing the pattern of indicia endoscopically.

In another aspect, the invention is a method of positioning and exchanging medical catheters within a bodily passage during a medical procedure which uses an endoscope. The method utilizes one of the above-described exchange guidewires in accordance with the invention, having a proximal end and a distal tip. The method involves positioning the exchange guidewire distal tip at a preselected position within the bodily passage; confirming the position of the exchange guidewire by fluoroscopically viewing the position of the radiopaque coil and/or core wire distal end portion; threading one of the catheters onto the exchange guidewire proximal end and moving this catheter along the exchange guidewire toward the exchange guidewire distal tip to position this catheter within the bodily passage; exchanging another of the catheters for the one catheter by withdrawing the one catheter from the bodily passage over the exchange guidewire, removing the one catheter from the exchange guidewire, threading the other catheter onto the exchange guidewire proximal end, and moving the other catheter along the exchange guidewire toward the exchange guidewire distal tip to position the other catheter within the bodily passage; and endoscopically monitoring movement of the exchange guidewire indicia relative to an optical lens of the endoscope during the exchange and preventing any significant degree of withdrawal of the exchange guidewire during exchange of the catheters.

BRIEF DESCRIPTION OF THE DRAWINGS

For a better understanding of the present invention, together with other objects, advantages, and capabilities thereof, reference is made to the following Description and appended Claims, together with the Drawings in which:

FIG. 1 is an elevation view of an exchange guidewire in accordance with one embodiment of the invention;

FIG. 2 is a view of a portion of the guidewire of FIG. 1, partly in cross-section;

FIG. 3 is an elevation view of a portion of an exchange guidewire, partly in cross-section, in accordance with another embodiment of the invention.

DETAILED DESCRIPTION OF THE PREFERRED EMBODIMENTS

An exemplary embodiment of the exchange guidewire in accordance with the invention is described herein. The guidewire has a core wire over most of its length, and a flexible coil attached to the distal end of the core wire. A flexible sleeve is closely fitted to and covers the core wire and the flexible coil over their entire length. The flexible sleeve is marked with a bi-color "zebra-stripe" pattern, having a background color and a continuous helical stripe of a contrasting color over the entire length of the sleeve. The background color, stripe color, and pattern are selected to be readily discernable when viewed endoscopically within a bodily passage.

The preferred core wire is a non-kinking metal alloy wire, for example a nickel titanium alloy wire such as, e.g., Nitinol ® alloy wire, about 0.010–0.050 in, preferably 0.012–0.038 in. in diameter, and is conveniently at least twice the length of the longest catheter to be threaded over the guidewire to enable gripping of the guidewire during withdrawal of a catheter to resist friction-induced movement of the guidewire. Typical total lengths for the guidewire are about 45–450 cm. Also preferred is gradual tapering at the distal end of the core wire before the tip to facilitate passage through tight strictures and small and tortuous bodily passages. Typically, the core wire is tapered, e.g. by grinding, over approximately 1–60 cm, preferably 5–35 cm of the distal end before the distal end portion within the guidewire distal tip. The minimum diameter of the tapered portion, and the diameter of the portion within the tip, may be as small as about 0.002–0.012 in, preferably 0.004–0.010 in.

Alternatively, other metals or alloys or other materials suitable for medical use may be used for the core wire, for example polymeric materials, but the core wire must be threadable through bodily passages without kinking.

The flexible coil is typically a helically wound single strand of radiopaque wire about 0.001–0.003 in. in diameter, the coil typically being close wound and of a diameter of at least about 0.010 in, preferably 0.016 in, and not significantly greater than the diameter of the core wire proximal end. Conveniently, the coil may be fabricated of platinum wire, and may be ball welded or otherwise fixedly attached to the distal end of the core wire to be coaxial therewith.

Alternatively, the tip could be made radiopaque by forming the coil from a polymeric material incorporating a radiopaque powdered material such as tungsten or platinum. Alternative methods of attaching the coil to the core wire are brazing, soldering, resistance welding, or using an adhesive, as appropriate to the materials being joined. The flexible coil and core wire distal end within it may be continuously coaxial with the proximal end and taper of the core wire, that is they may have a straight profile, or they may be bent, e.g. by heat treatment, into a partial "J" profile, as described more fully below. Also alternatively, the radiopacity could be applied to the distal end of the core wire, for example a platinum or gold plating, and a flexible coil attached over this radiopaque portion.

The sleeve or jacket over the wire/coil assembly is of a low-friction material suitable for medical use, for example Teflon. The sleeve may conveniently be applied by shrink wrapping a hollow tube of such material over the wire/coil assembly. Indicia suitable for viewing by endoscope are applied to the sleeve before or after application of the sleeve to the wire/coil assembly. Typical indicia are colored stripes over a contrasting background field, but any indicia axially spaced apart along the length of the guidewire, discernable by endoscope during an endoscopic procedure, and which will enable the surgeon to discern movement of the guidewire relative to the optical cable are suitable.

Alternatively, the indicia may be applied to the wire/coil assembly and a transparent sleeve applied for visibility of the indicia. Also alternatively, the sleeve may be omitted, and the guidewire may be the marked wire/coil assembly. The indicia may be one or more continuous helical stripes, individual discontinuous circumferential stripes, or other suitable indicia, as described above. The markings may be bi-color, i.e. a single color on a contrasting background (which may be the natural color of the untinted core wire), tri-color, or any combination of colors, including black and white, which are endoscopically discernable. The indicia typically are about 1–4 mm wide and are spaced apart about 2–4 mm for endoscopic clarity. In one embodiment, the indicia are radiotransparent for clarity of fluoroscopic viewing. The indicia described herein extend over the entire length of the guidewire, but need extend only over that portion of the guidewire to be monitored during the catheter exchange procedure, for example, over the most distal 60 cm, or over the tapered portion.

The sleeve or jacket may be shrink-wrapped as described above, or may be applied by, for example, spraying, dipping, etc. For certain procedures it may be advantageous to apply a coating of an additional low-friction, "slick" silicone or hydrophilic coating to the exchange guidewire, e.g. over the entire length or the most distal about 60 cm.

The following is a description of various illustrative embodiments of the invention shown in the Drawings. However, this description is not intended to limit the scope of the present invention, but merely to be illustrative and representative thereof.

FIG. 1, not to scale, illustrates guidewire 10, about 0.035 in. diameter×450 cm long. Guidewire 10 includes proximal portion 12, tapered portion 14 and distal tip 16. Tapered portion 14 and distal tip 16 total about 30 cm in length. Shrink-wrapped Teflon sleeve 18 extends over the entire length of guidewire 10, and is clipped close at each end, as shown at 20 and 22. Sleeve 18 displays background 24 in a first color, for example white, and continuous helical stripe 26 marked on the background in a contrasting color, for example blue, over the entire length of sleeve 18. An abrupt change in diameter is discernable at 28 between tapered portion 14 and tip 16.

FIG. 2, also not to scale, shows a portion of the guidewire of FIG. 1 in more detail, and partially in cross-section. In FIG. 2, features similar to those in FIG. 1 are indicated by the same reference numerals. Proximal portion 12 of guidewire 10 includes proximal end 30 of Nitinol ® alloy core wire 32, which in portion 12 is of a constant diameter D, and sleeve 18. Core wire 32 also includes distal end 34, within guidewire distal tip 16, and tapered portion 36, which is generally within guidewire tapered portion 14. Core wire taper 36 has been ground to taper down to a diameter of about ¼ D at distal end 34. Guidewire distal tip 16 also includes radiopaque, flexible, platinum coil 38. Coil 38 extends over the entire length of core wire distal end 34, resting against the smaller end of taper 36 and ball welded to most distal point 40 of core wire 32.

Core wire proximal end 30, taper 36, and coil 38 are covered by sleeve 18 from guidewire end 20 to end 22. Sleeve 18 is marked with stripe 26 on background 24 over its entire length from end 20 to end 22 of guidewire 10.

FIG. 3, again not to scale and partially in cross-section, illustrates another embodiment of the exchange guidewire described herein. In FIG. 3, features similar to those in FIGS. 1 and 2 are indicated by the same reference numerals. FIG. 3 shows guidewire 10a including a proximal portion (not shown), tapered portion 14 and distal tip 16a. Core wire 32 includes tapered portion 36 and a distal end (not shown) within guidewire distal tip 16a. Guidewire distal tip 16a also includes radiopaque, flexible, platinum coil 38a, which is ball welded to the core wire distal end at its most distal point. Coil 38a and the core wire distal end have been heat treated to maintain a bent, partial "J"-shaped curve 42 to aid manipulation of the tip into small openings and through tortuous bodily passages. Shrink-wrapped Teflon sleeve 18a extends over the entire length of guidewire 10a, in a manner similar to that shown for the guidewire of FIGS. 1 and 2. Sleeve 18a displays background 24a in a first color and individual, discontinuous, circumferential stripes 26a marked on the background in a contrasting color over the entire length of the sleeve.

In operation, the novel exchange guidewire having endoscopically discernable indicia visible at the surface of its low-friction jacket is threaded through a lumen in the endoscope. The guidewire is then maneuvered into place within a bodily passage to act as a guide for positioning of medical catheter devices to perform a desired medical procedure. The flexible coil, particularly the J-tip coil, and the low-friction Teflon® sleeve aid in the positioning of the guidewire within the bodily passage.

In an exemplary procedure, the endoscope is introduced orally and maneuvered through the alimentary canal into the duodenum. The guidewire is threaded through the endoscope lumen and manipulated by torquing, pushing, and pulling to cannulate the papilla and enter the common bile duct and, if necessary, any duct branching therefrom. The position of the guidewire is confirmed fluoroscopically. The guidewire distal tip includes a radiopaque material to aid fluoroscopic viewing of the guidewire position. After positioning of the guidewire within the duct, a catheter bearing a medical instrument is threaded onto the exposed end of the guidewire and maneuvered through the endoscope lumen, along the guidewire, and into position within the duct to be treated. The guidewire, the medical instrument catheter, and the area near the papilla all are illuminated by a fiber optic light source within the endoscope, and may be viewed through the endoscope using a fiber optic lens.

When a second or subsequent instrument is required to perform the medical procedure, the catheter is withdrawn from the bodily passage and the endoscope over the guidewire. A replacement catheter bearing the next-required instrument is threaded onto the guidewire and maneuvered into position.

The exchange guidewire bearing endoscopically discernable indicia, as described herein, has greatly simplified exchange of medical instrument catheters during endoscopic surgery and other endoscopic procedures, with shorter exposure to fluoroscopic radiation and shorter procedure time. The guidewire is useful in such endoscopic medical procedures as endoscopic surgery or other medical treatment within, for example, the common bile duct, the cystic duct, the pancreatic duct, or the left or right hepatic duct. The tendency for the guidewire to be displaced during the withdrawal of a catheter is easily controlled using the guidewire described herein, which provides a way to visually discern any such displacement of the guidewire during the exchange process without the use of further fluoroscopy.

While there has been shown and described what are at present considered the preferred embodiments of the invention, it will be apparent to those skilled in the art that modifications and changes can be made therein without departing from the scope of the present invention as defined by the appended Claims.

We claim:

1. An exchange guidewire for positioning and exchanging medical catheters within a bodily passage during a medical procedure which uses an endoscope, said guidewire comprising:

a core wire of a length sufficient for exchange of said catheters through said endoscope, said core wire having a proximal end about 0.01–0.05 inch in diameter and a distal end of a diameter no greater than that of said core wire proximal end;

a flexible coil about 1–10 cm long and of a diameter between about 0.01 inch and approximately the diameter of said core wire proximal end, at least a portion of at least one of said coil and said core wire distal end being radiopaque, said coil having a proximal end and a distal tip, said coil proximal end fixed to said core wire distal end to produce a wire/coil assembly;

a low-friction sleeve tightly fitted around and conforming to said wire/coil assembly to cover said wire/coil assembly from said core wire proximal end to said coil distal tip to form a jacketed guidewire; and a pattern of indicia along the entire length of said core wire, said sleeve being sufficiently transparent for said pattern to be endoscopically discernable through said sleeve so that the position of said exchange guidewire indicia relative to an optical lens of said endoscope may be monitored.

2. An exchange guidewire in accordance with claim 1 wherein said pattern of indicia is a striped pattern having a background color and striping of a contrasting color.

3. An exchange guidewire in accordance with claim 2 wherein said striped pattern is a helically striped pattern in which said striping comprises at least one continuous helical stripe.

4. An exchange guidewire in accordance with claim 2 wherein said striped pattern is a circumferentially striped pattern in which said striping comprises individual discontinuous circumferential stripes.

5. An exchange guidewire for positioning and exchanging medical catheters within a bodily passage during a medical procedure which uses an endoscope, said guidewire comprising:

a core wire of a length sufficient for exchange of said catheters through said endoscope, said core wire having a proximal end about 0.01-0.05 inch in diameter and a distal end of a diameter no greater than that of said core wire proximal end;

a flexible, radiopaque coil about 1-10 cm long and of a diameter between about 0.01 inch and approximately the diameter of said core wire proximal end, said coil having a distal tip fixed to said core wire distal end to produce a wire/coil assembly;

a low-friction sleeve tightly fitted around and conforming to said wire/coil assembly to cover said wire/coil assembly from said core wire proximal end to said coil distal tip to form a jacketed guidewire; and a pattern of indicia along the entire length of said low friction sleeve, said pattern being endoscopically discernable at the surface of said low friction sleeve;

so that the position of said exchange guidewire indicia relative to an optical lens of said endoscope may be monitored by viewing said pattern of indicia endoscopically.

6. An exchange guidewire in accordance with claim 5 wherein said pattern of indicia is a striped pattern having a background color and striping of a contrasting color.

7. An exchange guidewire in accordance with claim 6 wherein said striped pattern is a helically striped pattern in which said striping comprises at least one continuous helical stripe.

8. An exchange guidewire in accordance with claim 6 wherein said striped pattern is a circumferentially striped pattern in which said striping comprises individual discontinuous circumferential stripes.

9. A method of positioning and exchanging medical catheters within a bodily passage during a medical procedure which uses an endoscope, said method utilizing an exchange guidewire having a proximal end and a distal tip, said method comprising the steps of:

positioning said exchange guidewire distal tip at a preselected position within said bodily passage, said exchange guidewire comprising: (a) a core wire of a length sufficient for exchange of said catheters through said endoscope, said core wire having a proximal end about 0.01-0.05 inch in diameter and a distal end of a diameter no greater than that of said core wire proximal end; (b) a flexible coil about 1-10 cm long and of a diameter between about 0.01 inch and approximately the diameter of said core wire proximal end, at least a portion of at least one of said coil and said core wire distal end being radiopaque, said coil having a distal tip fixed to said core wire distal end to produce a wire/coil assembly; (c) a low-friction sleeve tightly fitted around and conforming to said wire/-coil assembly to cover said wire/coil assembly from said core wire proximal end to said coil distal tip to form a jacketed guidewire; and (d) a pattern of indicia along the entire length of said core wire, said sleeve being sufficiently transparent for said pattern to be endoscopically discernable through said sleeve so that the position of said exchange guidewire indicia relative to an optical lens of said endoscope may be monitored;

confirming the position of said exchange guidewire by fluoroscopically viewing the position of said radiopaque portion;

threading one of said catheters onto said exchange guidewire proximal end and moving said one catheter along said exchange guidewire toward said exchange guidewire distal tip to position said one catheter within said bodily passage;

exchanging another of said catheters for said one catheter by withdrawing said one catheter from said bodily passage over said exchange guidewire, removing said one catheter from said exchange guidewire, threading said another catheter onto said exchange guidewire proximal end, and moving said another catheter along said exchange guidewire toward said exchange guidewire distal tip to position said another catheter within said bodily passage; and endoscopically monitoring movement of said exchange guidewire indicia relative to an optical lens of said endoscope during said exchange step and preventing any significant degree of withdrawal of said exchange guidewire during exchange of said catheters.

10. A method in accordance with claim 9 wherein said pattern of indicia is a striped pattern having a background color and striping of a contrasting color.

11. A method in accordance with claim 10 wherein said striped pattern is a helically striped pattern in which said striping comprises at least one continuous helical stripe.

12. A method in accordance with claim 10 wherein said striped pattern is a circumferentially striped pattern in which said striping comprises individual discontinuous circumferential stripes.

13. A method in accordance with claim 9 wherein said bodily passage comprises the alimentary canal of a patient and said positioning step comprises the substeps of:

introducing said endoscope to said alimentary canal and maneuvering said endoscope through said alimentary canal into the duodenum;

threading said guidewire through a lumen of said endoscope to said duodenum and maneuvering said guidewire into the common bile duct and, optionally, into any duct branching from said common bile duct.

14. A method of positioning and exchanging medical catheters within a bodily passage during a medical procedure which uses an endoscope, said method utilizing an exchange guidewire having a proximal end and a distal tip, said method comprising the steps of:

positioning said exchange guidewire distal tip at a preselected position within said bodily passage, said exchange guidewire comprising: (a) a core wire of a length sufficient for exchange of said catheters through said endoscope, said core wire having a proximal end about 0.01-0.05 inch in diameter and a distal end of a diameter no greater than that of said core wire proximal end; (b) a flexible, radiopaque coil about 1-10 cm long and of a diameter between about 0.01 inch and approximately the diameter of said core wire proximal end, said coil having a distal tip fixed to said core wire distal end to produce a wire/coil assembly; (c) a low-friction sleeve tightly fitted around and conforming to said wire/coil assembly to cover said wire/coil assembly from said core wire proximal end to said coil distal tip to form a jacketed guidewire; and (d) a pattern of indicia along the entire length of said core wire, said pattern being endoscopically discernable;

confirming the position of said exchange guidewire by fluoroscopically viewing the position of said radiopaque coil;

threading one of said catheters onto said exchange guidewire proximal end and moving said one catheter along said exchange guidewire toward said exchange guidewire distal tip to position said one catheter within said bodily passage;

exchanging another of said catheters for said one catheter by withdrawing said one catheter from said bodily passage over said exchange guidewire, removing said one catheter from said exchange guidewire, threading said another catheter onto said exchange guidewire proximal end, and moving said another catheter along said exchange guidewire toward said exchange guidewire distal tip to position said another catheter within said bodily passage; and endoscopically monitoring movement of said exchange guidewire indicia relative to an optical lens of said endoscope during said exchange step and preventing any significant degree of withdrawal of said exchange guidewire during exchange of said catheters.

15. A method in accordance with claim 14 wherein said pattern of indicia is a striped pattern having a background color and striping of a contrasting color.

16. A method in accordance with claim 15 wherein said striped pattern is a helically striped pattern in which said striping comprises at least one continuous helical stripe.

17. A method in accordance with claim 15 wherein said striped pattern is a circumferentially striped pattern in which said striping comprises individual discontinuous circumferential stripes.

18. A method in accordance with claim 14 wherein said bodily passage comprises the alimentary canal of a patient and said positioning step comprises the substeps of:

introducing said endoscope to said alimentary canal and maneuvering said endoscope through said alimentary canal into the duodenum;

threading said guidewire through a lumen of said endoscope to said duodenum and maneuvering said guidewire into the common bile duct and, optionally, into any duct branching from said common bile duct.

* * * * *